US00PP35874P2

(12) United States Plant Patent
Chen

(10) Patent No.: US PP35,874 P2
(45) Date of Patent: Jun. 18, 2024

(54) ***EPIPREMNUM* PLANT NAMED 'UF-Ea-0317'**

(50) Latin Name: *Epipremnum aureum*
Varietal Denomination: UF-Ea-0317

(71) Applicant: Florida Foundation Seed Producers, Inc., Marianna, FL (US)

(72) Inventor: Jianjun Chen, Lake Mary, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/371,574

(22) Filed: Sep. 22, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP20,930 P2 4/2010 Henny et al.
PP21,217 P2 8/2010 Henny et al.

*Primary Examiner* — Susan McCormick Ewoldt
*Assistant Examiner* — Zachariah Allan Kay
(74) *Attorney, Agent, or Firm* — Koenig IP Works, PLLC; Katherine Koenig

(57) ABSTRACT

A new and distinct cultivar of Pothos (*Epipremnum aureum*) plant named 'UF-Ea-0317', particularly distinguished by aristate shaped leaves having a consistent light green coloration outlined by yellow venation cross the entire leaf surface, medium size plant form, semi-compact and trialing growth habit, and yellow green stems, is disclosed.

3 Drawing Sheets

Genus and species: *Epipremnum aureum.*
Cultivar denomination: 'UF-Ea-0317'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

*Epipremnum* Schott, commonly known as Pothos, belongs in the family Araceae and is native to the southeast Asian and Solomon Islands in the Pacific. *Epipremnum* has about 10 species, but only *E. aureum* or *E. pinnatum* 'Aureum' (Boyce, 1998) has been widely grown as an ornamental and is among the most popular foliage plants worldwide. Pothos is an important foliage plant in the commercial trade. Based on the USDA Floriculture Crops Statistics, the wholesale value of Pothos in 2018 was $22.89 million. It ranked as the third among all cultivated foliage plant genera. With the increased popularity of "living walls" since 2010, pothos has been the highest in-demand indoor foliage plant, especially demand for cultivars with contrasting and bright foliage colors. Prior to 2009, there have been only four cultivars available in commercial trade, 'Golden Pothos' (unpatented), 'Marble Queen' (unpatented), 'Jade' (unpatented), and 'Neon' (unpatented). In 2009, two new Pothos cultivars were released, namely, 'UFM10' (U.S. Plant Pat. No. 20,930, commercial name Green Genie™, owned by Florida Foundation Seed Producers, Inc.) and 'UFM12' (U.S. Plant Pat. No. 21,217, commercial name Pearls and Jade®, registered trademark of Florida Foundation Seed Producers, Inc.). These two cultivars are the result of mutation breeding through exposure to gamma ray radiation.

Pothos has bisexual flowers like its relatives of *Anthurium* and *Spathiphyllum* but rarely flowers in nature. Thus, Pothos is propagated predominantly through single or double eye stem or vine cuttings. As a result, there have been no literature reports of Pothos breeding through hybridization. Since Pothos breeding through conventional hybridization is difficult, a new method was initiated for developing new pothos cultivars through selection of mutants from regenerated populations. Pothos was first successfully regenerated from leaf and petiole explants in 2002, and subsequently, methods for regeneration of 'Golden Pothos' through direct somatic embryogenesis was accomplished in 2005, 'Marble Queen' in 2012, as well as other Pothos cultivars. The established regeneration systems were used for isolation of mutants.

SUMMARY OF THE INVENTION

The invention relates to a new and distinct cultivar of Pothos plant named 'UF-Ea-0317'. The new cultivar 'UF-Ea-0317' originated from a regenerated population of 'Golden Pothos'. Leaf explants of 'Golden Pothos' were cultured on Murashige and Skoog (MS) medium supplemented with 8 μM N-(2-chloro-4-pyridl)-N'-phenylurea (CPPU) and 1 μM α-naphthalene acetic acid (NAA). Somatic embryos directly occurred on the leaf surface and on the cut ends in 4-6 weeks. Subsequent embryo conversion resulted in plantlets four to six weeks later. Plantlets with unique leaf variegation were selected and transplanted into plug trays filled with a substrate in a shaded greenhouse for acclimatization. Selected plants were potted in 15-cm pots for evaluation. 'UF-Ea-0317' was selected as a single plant from said regenerated population in March 2014 in Apopka, Florida due to its unique leaf shape and leaf color patterning.

The new cultivar 'UF-Ea-0317' was first propagated asexually by vegetative stem cuttings in August 2014 in Apopka, Florida and has been found to remain true-to-type and to retain its distinctive characteristics through successive asexual propagations for eight years.

Plant Breeder's Rights for the new cultivar 'UF-Ea-0317' have not been applied for, and 'UF-Ea-0317' has not been made publicly available more than one year prior to the filing date of this application.

The new cultivar 'UF-Ea-0317' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF-Ea-0317' when grown under normal horticultural practices in Apopka, Florida: Aristate shaped leaves having a consistent light green coloration outlined by yellow venation cross the entire leaf surface; medium size plant form; and semi-compact and trialing growth habit.

When compared to the parent Pothos plant 'Golden Pothos' (unpatented), 'UF-Ea-0317' is a medium size plant with leaves having a consistent light green coloration outlined by yellow venation, whereas 'Golden Pothos' is a larger size plant with leaves having a more marbled, dark green and yellow coloration in patches. Additionally, 'UF-Ea-0317' has yellow-colored stems, whereas 'Golden Pothos' has green-colored stems.

DESCRIPTION OF THE FIGURES

This new Pothos cultivar 'UF-Ea-0317' is illustrated by the accompanying photographs, which show the plant's form and foliage. The colors shown are as true as can be reasonably obtained by conventional photographic procedures. The photographs are of five-month old plants grown from unrooted cuttings in March 2018 in a shaded greenhouse in Apopka, Florida.

DETAILED BOTANICAL DESCRIPTION OF THE CULTIVAR

Figure 1:
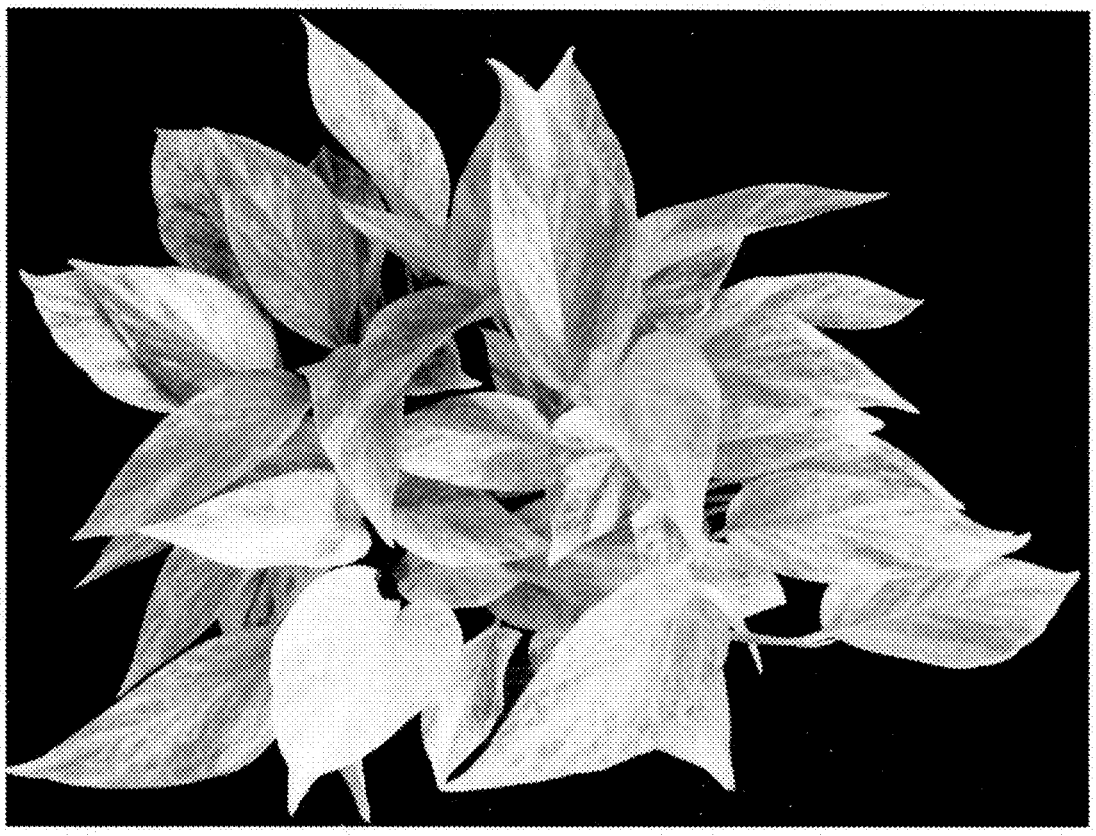
FIG. 1 shows the growth habit, form, and foliage of the new Pothos cultivar 'UF-Ea-0317'.
Figure 2:
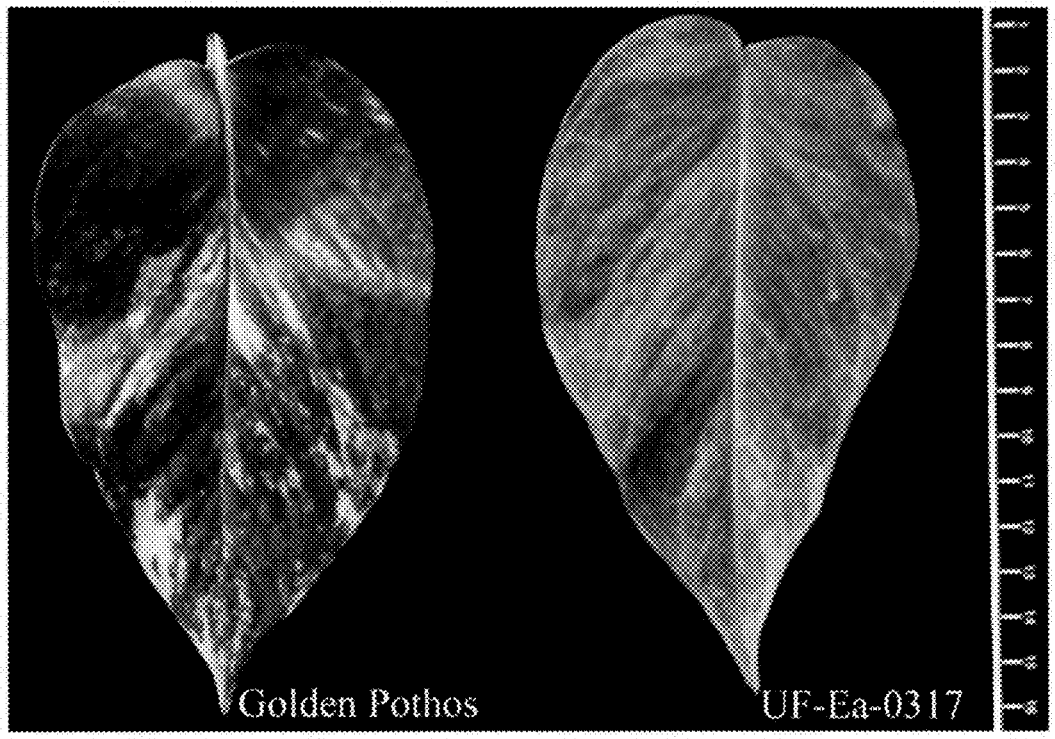
FIG. 2 shows a side-by-side comparison of the adaxial surface of a leaf of 'UF-Ea-0317' (right) and 'Golden Pothos' (left)
Figure 3:
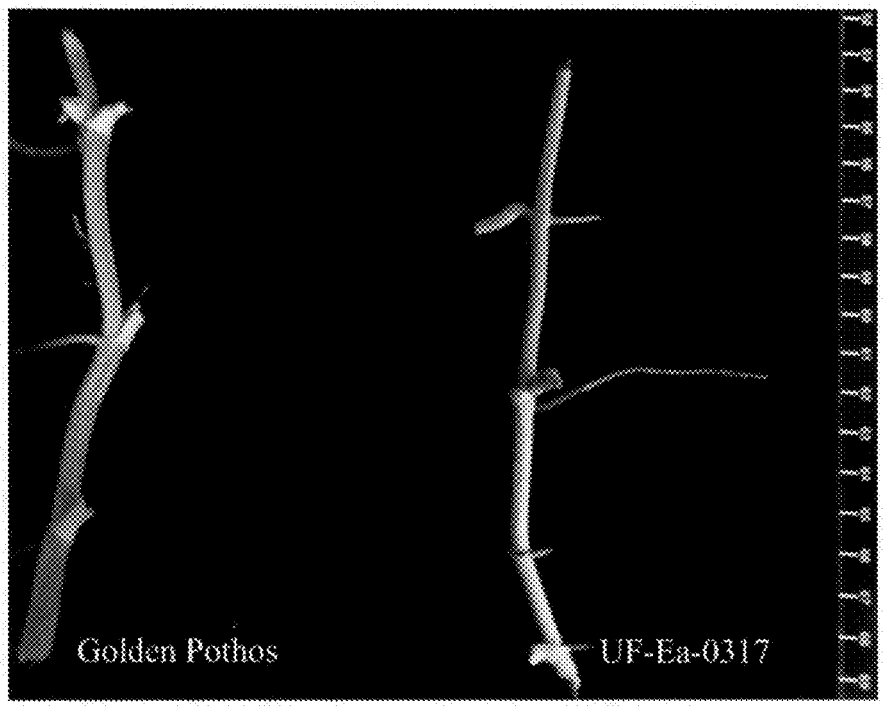
FIG. 3 shows a side-by-side comparison of a stem of 'UF-Ea-0317' (right) and 'Golden Pothos' (left).

Foliage color was determined under full sun conditions in the middle of the day in a shaded greenhouse with 75% light exclusion. Color references are to The R.H.S. Colour Chart of The Royal Horticultural Society of London (R.H.S.), 2007 5$^{th}$ Edition. The following detailed description of 'UF-Ea-0317' was obtained using six-month old plants grown from unrooted cuttings in March 2018 in a shaded greenhouse in Apopka, Florida. The plants were propagated in mist for 2-3 weeks after cuttings were stuck, then grown in 20-cm (8") diameter pots with approximately 20 cuttings per pot for approximately 23 additional weeks.

BOTANICAL DESCRIPTION

Botanical classification:

*Family*.—Araceae.

*Botanical name*.—*Epipremnum aureum*.

*Common name*.—Pothos.

*Cultivar*.—'UF-Ea-0317'.

Plant description:

*Plant type*.—Perennial tropical vine.

*Growth habit*.—Slightly compact and trailing.

*Height from soil level to top of foliar plane*.—Approximately 22 cm.

*Growth rate*.—Fast.

*Branching characteristics*.—One main stem (vine), weak basal branching.

*Vine length*.—Approximately 45 cm on a 3-month-old plant.

*Vine diameter*.—Approximately 0.4 cm.

*Internode length*.—5 to 6 cm on a 3-month-old plant.

*Texture of vines*.—Glabrous and striated.

*Shape of vines*.—Round and slightly flat.

*Color of vines*.—Mature vines are yellow green (10D) with some green (140C) linear striations, and young vines upper side are greenish (141C) and lower side are light green (142B).

*Number of leaves per vine*.—8 to 9 on a 3-month old plant.

Propagation:

*Type cuttings*.—Vegetative stem cuttings having at least 1 node.

*Time to initiate roots*.—21 days.

*Time to produce a rooted cutting*.—20 weeks.

*Root habit*.—One aerial root oriented downwards and present at each stem node, aerial roots produce fine roots when in contact with soil.

*Root description*.—Aerial roots are about 3 cm in length and 2 mm in diameter, colored brown (165A), soil roots are about 0.5 mm in diameter and colored white (NN155D).

Foliage description:

*Arrangement*.—Alternate.

*Attachment*.—Petiolate.

*Leaf*.—Shape: Aristate. Length: Approximately 12 cm. Width: Approximately 8 cm. Apex shape: Broadly acuminate. Base shape: Slightly cordate. Texture (upper surface): Glabrous and leathery. Texture (lower surface): Glabrous and leathery. Orientation: Newly expanded leaves are held erect and slightly upwards, mature leaves are more horizontal. Margins: Entire. Color: On mature leaves, green (143A) and yellow (10A); the interveinal areas are green (143A), but major veins and secondary veins are yellow (10A); young and recently fully expanded leaves have a distinct contrast between the two colors, whereas the green color in older leaves shows some fading to light yellow (10D) with irregular greenish (141D) striations; some older leaves may show irregular yellow-green (150C) blotches; the variegation in young leaves is visible on the adaxial surface only but becomes visible on both sides of mature leaves. Leaf sheen: Upper surface: Shiny. Lower surface: Shiny. Venation: Pattern: Eucamptodromous. Color: Upper surface: Yellow (3A). Lower surface: Light yellow (2C).

*Petiole*.—Length: 8 to 9 cm. Width: Approximately 0.4 cm. Color: Yellow green (151C) with some green (141C) linear striations.

Inflorescence: None observed to date.
Fruit and seed set: None observed to date.
Disease and insect resistance: None observed to date.
Cold tolerance: Tolerant down to 5° C.
Drought tolerance: Tolerant.

COMPARISON WITH KNOWN CULTIVARS

'Golden Pothos' (unpatented) is the best commercial comparison. When compared to 'Golden Pothos', the new cultivar 'UF-Ea-0317' is a medium size plant with leaves having a consistent light green coloration outlined by yellow venation, whereas 'Golden Pothos' is a larger size plant with leaves having a more marbled, dark green and yellow coloration in patches. Additionally, 'UF-Ea-0317' has yellow-colored stems, whereas 'Golden Pothos' has green-colored stems.

What is claimed is:

1. A new and distinct *Epipremnum* plant named 'UF-Ea-0317' as illustrated and described herein.

* * * * *